United States Patent [19]

McDaniel, Jr. et al.

[11] Patent Number: 4,904,774
[45] Date of Patent: * Feb. 27, 1990

[54] DECOLORIZATION OF GLYCOSIDES

[75] Inventors: Robert S. McDaniel, Jr.; Patrick M. McCurry; Rolland W. P. Short; Paul R. Glor, all of Decatur, Ill.

[73] Assignee: Henkel Kommanditgesellschaft auf Aktien, Duesseldorf, Fed. Rep. of Germany

[*] Notice: The portion of the term of this patent subsequent to Aug. 9, 2005 has been disclaimed.

[21] Appl. No.: 185,016

[22] Filed: Apr. 22, 1988

Related U.S. Application Data

[63] Continuation of Ser. No. 674,109, Nov. 21, 1984, Pat. No. 4,762,918.

[51] Int. Cl.$^4$ .................................................. C07H 1/06
[52] U.S. Cl. ...................................... 536/127; 536/124
[58] Field of Search ......................... 536/124, 127, 4.1

[56] References Cited

U.S. PATENT DOCUMENTS 4,483,979 11/1984 Mao ..................... 536/127
4,762,918 8/1988 McDaniel, Jr. et al. .......... 536/127

Primary Examiner—Johnnie R. Brown
Assistant Examiner—Elli Peselev
Attorney, Agent, or Firm—Ernest G. Szoke; Wayne C. Jaeschke; Daniel S. Ortiz

[57] ABSTRACT

The catalytic hydrogenation of a glycoside composition to reduce the color of the composition is disclosed.

12 Claims, No Drawings

DECOLORIZATION OF GLYCOSIDES

This application is a continuation of U.S. application Ser. No. 06/674,109 which was filed Nov. 21, 1984, now U.S. Pat. No. 4,762,918.

BACKGROUND OF THE INVENTION

1. Field of the Invention.

This patent deals with the decolorization of glycosides which are useful as surfactants and for other purposes.

2. Description of the Art.

Glycosides are known to have several uses including their incorporation into detergent products as nonionic surfactants. Lower glycosides, that is those materials having a short hydrophobic moiety attached to the saccharide backbone as later described, are useful as intermediates for manufacturing higher glycosides. The lower glycosides are also useful for such purposes as mold release agents, for polymers which require a hydroxyl functionality, and as a formaldehyde scavenger in various products which utilize formaldehyde as a reactant.

Glycosides are typically formed from a lower saccharide which may be either monomeric or polymeric with regard to the saccharide unit. For reasons which are not fully understood the glycosides obtained from most processes are dark colored. The color ranges from dark yellow to coffee black depending upon the conditions under which the glycoside is produced. The color is not inherent to the glycoside per se but rather to the presence of humins which are co-produced with the glycoside.

It has been suggested that the color bodies (humins) in the glycoside composition may be removed by adsorption with resinous components. This process requires that the entire glycoside composition be mixed with a resin in sufficient volume to substantially remove the color forming materials.

It has also been suggested that the color bodies present in a glycoside composition may be eliminated by treatment with various reducing acids. The acid reduction has its limitations in that the acidic material must be neutralized or removed from the end products. This is the case with laundry detergents. Typically laundry detergent products are formulated in the alkaline pH range to facilitate removal of body soil. Thus while there is some market for glycosides in the acid pH range it is desired not to incorporate any more acid than is necessary. For a description of the use of reducing acids to produce glycosides see European Patent Application No. 82305286.5 to Arnaudis published as 0 077 167 on April 20, 1983.

Further discussion of treating a glycoside composition to reduce color is found in European Patent Application No. 83200572.2 to Mao published as 0 092 875 on November 2, 1983. In Mao the acid catalyst employed is stated to be destroyed after at least 90% of the short chain alkyl monosaccharide (glycoside) has been destroyed and before the average polysaccharide chain length exceeds about 20. U.S. Pat. No. 4,393,203 to Leslie issued July 12, 1983 describes the treatment of glycosides with a wipe film evaporator to assist in color reduction. Rau in U.S. Pat. No. 4,465,828 issued August 14, 1984 suggests using hydroxy carboxylic acids to minimize color formation when preparing glycosides.

A general method of preparing glycosides is found in U.S. Pat. No. 3,219,656 to Boettner issued November 23, 1965. Descriptions of producing alkyl glycosides are also found in U.S. Pat. No. 3,547,828 to Mansfield issued December 15, 1970 and U.S. Pat. No. 3,598,865 to Lew issued August 10, 1971. Roth also describes the preparation of glycosides in U.S. Pat. No. 4,223,129 issued September 16, 1980.

It is also known that glycosides may be decolorized by using a bleaching material. Suitable bleaches include materials such as hydrogen peroxide for bleaching. It has been observed, however, that upon exposure to high temperature, a bleached glycoside product can revert to a darker color product upon standing.

Hydrogenation of saccharides to form polyols has been known as evidenced by Kool in U.S. Pat. No. 2,609,399 issued September 2, 1952. It is not the intent of the present invention to form polyols by hydrogenation as this destroys the ketone and aldehyde functionality desired for glycoside formation.

It has now been discovered that the catalytic hydrogenation of a glycoside composition can substantially reduce the color. The hydrogenation of the glycoside composition of the present invention allows for considerably greater stability after color removal than does bleaching. That is, the hydrogenation of the color forming bodies in the glycoside composition leads to a more stable product than does the bleaching which gives products capable of reversible reactions.

Throughout the specification and claims percentages and ratios are by weight, temperatures are degrees Celsius and pressures are in KPascals unless otherwise indicated. To the extent that any of the references mentioned in this application are applicable to the present invention they are herein incorporated by reference.

SUMMARY OF THE INVENTION

This invention comprises a process for reducing the color of a glycoside composition including contacting the glycoside composition under hydrogenation conditions with a hydrogenation catalyst in the presence of hydrogen for a sufficient time to decrease the color thereof and thereafter separating the hydrogenation catalyst from the glycoside composition and recovering the glycoside composition of reduced color.

The invention also describes a glycoside composition containing hydrogenated humins.

DETAILED DESCRIPTION OF THE INVENTION

The glycoside may be obtained through, for example, the Mansfield, Lew, Boettner or Roth patents previously incorporated by reference. A glycoside is a material containing a saccharide structure which may be represented by the formula $$R(OG)_x$$

where R is a hydrophobic moiety, O an oxygen atom and (G) is the saccharide structure (backbone) of the glycoside. The value x is the number of monosaccharide units in the glycoside.

The oxygen atom shown in the formula above is typically derived from an alcohol with R being the hydrophobic moiety of the alcohol. The oxygen atom is attached to the saccharide in an ether linkage. Where the aldehyde or ketone structure of the saccharide is involved in the glycoside formation the product may be termed an acetal or ketal respectively. The favored reaction is the acetal or ketal formation to give the glycoside with the oxygen being attached to the carbon in the one position. It is less likely that the hydrophobic moiety will be attached through one of the remaining hydroxyl groups present on the starting saccharide.

Suitable hydrophobic moieties which are attached to the saccharide as previously described include primary or secondary alcohols having straight or branched chains which can be either saturated or unsaturated and may contain ether linkages. Preferably, the alcohols are primary saturated alcohols. Examples of such materials include those alcohols containing from 1 to about 30, preferably from about 1 to about 20, and most preferably from about 2 to about 18 carbon atoms. Specific alcohols which may be utilized herein include methyl, ethyl, propyl, isopropyl, butyl, pentyl, hexyl, heptyl, octyl, nonal, decyl, undecyl, dodecyl, tridecyl, tetradecyl, pentadecyl, hexadecyl, heptadecyl, and octadecyl.

Further alcohols which may be utilized herein include benzyl alcohol, phenol, and the sterol alcohols including cholesterol, sitosterol, stigmasterol, and the like. Also valuable herein are alcohols containing both an aromatic and aliphatic structure such as nonylphenol. Similarly, alkoxylated alcohols may be utilized which include materials such as the ethylene and propylene oxide adducts of any of the aforementioned alcohols or the polymerized forms of the aforementioned oxides, e.g. polyethylene glycol or polypropylene glycol.

The glycosides which are suggested for use in the present invention include those selected from the group consisting of fructoside, glucoside, mannoside, galactoside, taloside, aldoside, altroside, idoside, arabinoside, xyloside, lyxoside and riboside and mixtures thereof. Preferably the glycoside is a fructoside and most preferably a glucoside. All of the aforementioned glycosides may be obtained from sugars (saccharides) with the preferential fructose and glucose starting materials being obtained from corn syrup. Complex glycosides, those containing one or more different saccharide units, may also be used as starting materials.

The glycoside has the ability to utilize the monomeric saccharide unit to promote chain growth of the glycoside. Thus x in the above formula may vary between 1 and 10, preferably from about 1.2 to about 5, and most preferably from about 1.3 to about 3.5. The value x, may also be referred to as the degree of polymerization (D.P.) of the glycoside. This number is an average degree of polymerization. In obtaining a glycoside, polymerization of the monosaccharide units occurs to some extent usually through a 1,6 linkage. The saccharide portion of the glycoside molecule enhances water solubility and thus for detergent purposes it is advantageous to have the D.P. somewhat greater than 1. It is also desirable for detergents that the hydrophobic moiety have sufficient length to give a proper HLB e.g. $C_4$ and above.

Inherent in the glycoside formation is the generation of color bodies referred to as humins which are believed to be polymers of levulinic acid, furfural or hydroxymethyl furfural. The monomers of these polymers are obtained as a by-product when the saccharides are partially degraded by heat or other processing conditions. These monomers are then polymerized through a not fully understood mechanism into polymers which contain conjugated unsaturation which strongly absorbs light in the visible range. The removal of such components is extremely difficult. The reversibility of the glycoside formation to give an alcohol and the starting saccharide allows the generation humins throughout the process. Thus the practice of this invention is preferred over pretreating the saccharide or even intermediate glycosides to remove or eliminate the color forming bodies.

The glycoside within the glycoside composition is typically present on a dry solids basis during the hydrogenation reaction at from about 10% to about 75%, preferably from about 20% to about 60% by weight of the composition to be hydrogenated. The remainder of the glycoside composition includes saccharides, alcohols, water or other convenient solvents.

The hydrogenation catalyst employed herein may be any material suitable for such purpose. As the materials involved are organic, and for the most part carbohydrates, it is desirable that the catalyst be sufficiently active to allow saturation of the conjugated double bonds present in the glycoside composition. One skilled in the art in selecting the catalyst should be aware of the potential for the poisoning or inactivation of the catalyst by the glycoside or trace components within the glycoside composition.

The hydrogenation catalysts employed herein are typically selected from groups IB, IIIB, IVB, VI, VII and VIII of the periodic table. Conveniently the catalysts are based on nickel, platinum, palladium, molybdenum, chromium, osmium, iron, rhodium, cobalt, copper, silicon, platinum, aluminum, silver, manganese, lead, tin, rhenium, gallium, yttrium, lanthanum, and other rare earths and cerium and mixtures thereof.

The preferred catalysts which are employed herein are based on nickel, platinum, palladium, cobalt, and molybdenum. Furthermore, the hydrogenation catalyst may employ combinations of the foregoing metals to provide a balance of activity and selectivity. For example, a promoter may be used selected from the group consisting of molybdenum, chromium, osmium, iron, rhodium, rhenium, cobalt, copper, silicon, platinum, aluminum, silver, manganese, yttrium, lanthanum, and other rare earths and cerium and mixtures thereof. In addition, unwanted side reactions such as isomerization and decomposition to carbonaceous materials, etc. may be suppressed by the use of attenuators such as phosphorous, gallium, germanium, tin, lead, and sulfided forms of the active metals. Where desired the catalyst may be reduced and sulfided prior to its use. This may be accomplished during its synthesis or in situ prior to admixing with reactants.

Most conveniently the hydrogenation catalyst will be employed with a direct source of hydrogen to maintain the reaction and the catalyst in its active state. By maintaining the catalyst in its active state the process of decolorizing a glycoside composition may be conducted on a continuous basis. It is noted that some catalysts such as Raney nickel contain hydrogen within the structure of the catalyst and thus may be used without additional hydrogen. Of course, Raney nickel may also be used with added hydrogen such that the catalyst is maintained effective for longer periods of time. It is suggested that when conducting the reaction on a continuous basis that the catalyst be continuously removed and replaced with fresh amounts of catalyst to continue optimum processing.

The source of hydrogen is most conveniently hydrogen gas although other sources of hydrogen may be utilized such as lithium aluminum hydride or sodium borohydride.

The catalyst employed in the present invention may be supported or unsupported and may be utilized in a heterogeneous or homogeneous catalytic system. Most preferably, the catalysts employed herein are heterogeneous catalysts. In a heterogeneous catalyst system the catalyst constitutes a separate phase. Supported catalysts are always heterogeneous catalysts, however, heterogeneous catalysts also exist which are not supported. For example, a Raney nickel may be employed in a supported function or may be dispersed throughout the glycoside composition. One aspect of the present invention allows the catalyst to be utilized in a fixed bed which is in fact a heterogeneous supported catalyst system. In a preferred embodiment, the catalyst of this invention is employed in one or more fixed bed reaction zones through which the reactants are passed on a continuous basis and in the presence of hydrogen.

The use of hydrogen as previously described is typically carried out at from ambient pressure (101 KPa) to about 10,000 KPa. Preferably the hydrogen pressure will be from about 101 KPa to about 2,000 KPa. In practice the process may be conducted by maintaining sufficient hydrogen at the catalytic site to sustain the reaction.

The parameters of conducting a hydrogenation reaction may vary substantially in the present invention due to the selection of the catalyst for this particular hydrogenation reaction. These factors include, the amount of the color bodies (humins) in the glycoside composition to be hydrogenated; the partial pressure of the hydrogen gas (which determines concentration in the reaction phase); the temperature in the reaction vessel; the activity and amount of the catalyst utilized; and the duration of the contact of the glycoside composition with the catalyst and hydrogen. The degree of color improvement sought is also a factor. In practice, the dark brown state of the glycoside composition is conveniently converted to at least a straw yellow or amber liquid by the hydrogenation. As the glycosides have several uses, it is entirely possible during production to separate streams of the glycosides and to decolorize each stream to the desired extent depending upon the end usage.

The temperature of the glycoside composition during the hydrogenation is conveniently maintained between about 10° C. and 250° C., preferably from about 25° C. to about 120° C., most preferably from about 30° C. to about 90° C. As the function of the catalyst is to lower the activation energy for the hydrogenation reaction, the exact parameters of temperature are dependent upon the hydrogenation catalyst employed and the hydrogen concentration. It is desired to operate in the lower temperature ranges for hydrogenation. Low temperature operations on the glycoside composition are desired to minimize side reactions including the formation of further humins during the hydrogenation. Hydrogenolysis of the glycoside is also minimized by low temperatures.

The following are suggested hydrogenation catalysts which may be employed in the present invention. These catalysts include palladium on carbon; palladium on alumina or calcium carbonate; platinum on alumina; platinium on carbon; sulfided palladium on carbon; palladium on barium sulfate; palladium on barium carbonate powder; ruthenium on carbon; nickel, cobalt or molybdenum alone, or in combination, and on alumina; ruthenium on alumina; and rhodium on carbon and rhodium on alumina.

The following catalysts may be utilized in a pelleted or granular form. These catalysts include palladium on 4–8 mesh granular carbon, palladium on ⅛ inch alumina pellets, palladium on 28–150 mesh carbon. Platinum (sulfided) on 0.32 cm (⅛ inch) alumina pellets, ruthenium on 4–8 mesh granular carbon, ruthenium on 0.32 cm alumina pellets and rhodium on 0.32 cm alumina pellets. In addition to the foregoing iridium may be employed on a support which is carbon, calcium carbonate or alumina.

The following unsupported powdered catalysts may also be employed herein. These catalysts include palladium oxide, palladium black, platinum oxide, platinum black and ruthenium dioxide.

Metals of Group VIII which are conveniently used herein are iridium trichloride in the form of its hydrates, and osmium tetroxide. Palladium compounds usable herein include ammonium palladium (IV) hexachloride, palladium (II) chloride; palladium (II) diamino dichloride, palladium diamino dinitrite, palladium (II) nitrate, sodium palladium (II) chloride, and palladium (II).

Frequently used metal catalyst compounds include ammonium platinum (IV) hexachloride, chloroplatinic acid, platinum (II), platinum diamino dinitrite; potassium platinum (II) tetrachloride and potassium platinum (IV) hexachloride. Also useful herein are rhodium trichloride in the form of its hydrates, ruthenium dioxide, ruthenium nitrate, ruthenium trichloride and rhenium.

The following nickel catalysts from Alfa (Morton Thiokol) are useful herein: Nickel coated aluminum; nickel coated diatomaceous earth; nickel coated graphite; nickel on kieselguhr skirts; nickel on silica alumina; nickel molybdate on alumina; nickel, cobalt, iron oxide on alumina; nickel oxide on silica-alumina; nickel, tungsten on silica-alumina.

Metal powders of the Raney type-aluminum alloys are also useful herein. Such materials are the powdered alloys of aluminum with a base metal. The aluminum is leached with a strong caustic solution followed by careful water washing in the absence of air. These so-called Raney type catalysts are finely divided powders which are pyrophoric when exposed to the air. The typical aluminum-metal ratio in the alloy is 1:1. Such alloys include aluminum-cobalt; aluminum-copper and aluminum-nickel. These materials may be preactivated and stabilized so that they are non-pyrophoric. Of course, Raney nickel of the pyrophoric type may also be utilized, however, this material should be handled to avoid contact with free oxygen.

The following disclosure of catalysts suitable herein is found in *Catalysis of Organic Reactions* edited by William R. Moser published by Marcel Dekker, Inc. copyright 1981 New York and Basel. (Pages 383 et seq.)

Further disclosures of suitable catalysts herein include Raney-type nickel catalysts prepared from a ternary nickel-silicon-cobalt alloy. Similarly, nickel-aluminum-molybdenum, nickel-aluminum-cobalt and nickel-aluminum-chromium alloys are also useful herein. Further ternary alloys of interest include those of Ishikawa reported at *Nippon Kagaku Zasshi* 81 (1960) and 82 (1961). Ishikawa describes ternary alloys of silver, copper, iron, manganese, lead and tin. Further descriptions in the *Catalysis of Organic Reactions* include quaternary and quinary alloys.

The following materials described in *Raney Active Metal Catalysts and Alloys* of the Davison Chemical Division of W. R. Grace & Company are also useful herein. These products described as Raney active catalysts include Raney 2400-chromium-promoted; Raney 27-cobalt; Raney-28-nickel; Raney-29-copper, Raney-30-molybdenum-promoted; Raney 3000-molybdenum-promoted; Raney 200-nickel (highly active nickel fines); Raney 4100-nickel; Raney 4200-nickel; and Raney 4300-molybdenum-promoted.

Raney alloys also available from W. R. Grace include 2413-chromium-promoted nickel-aluminum powder; 2713-cobalt-aluminum powder; 2813-nickel-aluminum alloy powder; 2913-copper-aluminum alloy powder; 5842-crushed-granular nickel-aluminum alloy; and 5830-crushed granular molybdenum promoted nickel aluminum. The catalysts found in *Raney Active Metal Catalysts and Alloys* Davison Chemical Division, W. R. Grace & Company are herein incorporated by reference.

Further suggested hydrogenation catalysts include those described in Volume 2, *A Bibliography of Research in Catalysis with the Rare Earth Elements* (1971–1976) entitled Application Report 7907 Molycorp, Inc. 6 Corporate Park Drive, White Plains, New York 10604 pages 19–21. Still further discussions on the preparation of Raney nickels W2; W4; W6; W7; and W8 for deuteration are discussed in *Catalytic Hydrogenation Techniques and Applications in Organic Synthesis*, Robert L. Augustine 1965, Marcel Dekker, Inc. which is herein incorporated by reference. The disclosures on the preparation of Raney nickel catalyst by Augustine are found in the appendix at pages 147–149. Other useful Raney catalysts include W1; W3; and W5.

The catalyst may be separated from the glycoside composition following hydrogenation by any convenient means such as filtration, decanting, or using a support. The glycoside is thus recovered in a less colored state.

The following are suggested exemplifications of the present invention.

EXAMPLE I

A suggested exemplification of the present invention involves the treating of a glycoside composition comprising n-butyl glucoside which is prepared from starch according to the Roth patent previously incorporated herein by reference.

The n-butyl glucoside in the amount of 100 parts (28.29 parts solids in butanol) is placed in a reaction vessel containing 0.52 parts of 20% aqueous sodium hydroxide. Also present in the hydrogenation vessel are 1.47 parts of wet Raney nickel. The system is sealed such that the later described hydrogen gas will not be vented to the atmosphere.

The hydrogen gas is generated in this experiment by introducing sodium borohydride (dissolved in aqueous sodium hydroxide) to a second reaction vessel containing sufficient 5N sulphuric acid to generate the required amount of hydrogen gas. In the present case, the hydrogen gas is generated over a sufficient period of time to obtain the maximum color reduction possible in the glucoside. A conduit is employed between the reaction vessel which is generating the hydrogen gas and the reaction vessel containing the butyl glucoside. Sufficient agitation is maintained in each vessel so that the hydrogen gas is evolved, and second, adequately dispersed in the butyl glucoside composition. The initial reaction is conducted over a period of approximately $3\frac{1}{2}$ hours at 25° C. The reaction mixture is then treated for an additional four hours at from 70° C. to 75° C. to increase the amount of hydrogen gas reacted in the glucoside composition.

The hydrogenated glucoside composition is then tested for transmittance using a 2 centimeter cell at 470 nanometers.

The improvement over the starting glucoside compared to the end hydrogenated glucoside composition showed a 62% transmittance increase.

EXAMPLE II

A second glucoside composition is prepared as in Example I with the exception that the caustic is omitted in the vessel containing the glucoside and the catalyst is platinum on charcoal. The amount of catalyst employed is 0.1 part of 5% platinum on charcoal.

The reaction is conducted at from about 70° C. to 75° C. over a period of 6 hours. The color reduction of the glucoside mixture is visibly noticeable.

An as is color comparison of the starting glucoside to the hydrogenated end-product shows a transmittance increase of greater than 100%.

Example II is repeated by dispersing the glycoside prior to hydrogenation in 5 parts of butyl alcohol per part of glycoside. The hydrogenated composition will have approximately the same color as in Example II but will be easier to process due to a more fluid nature.

EXAMPLE III

The hydrogenation of the glucoside composition of Example I may be repeated utilizing any of the hydrogenation catalysts listed in the Detailed Description of the Invention. The glucoside compositions are observed to be improved in color as a result of the hydrogenation.

A further variable in the present invention is to use Raney nickel in a batch process where no outside hydrogen gas is included. A further variation of the present invention is to utilize hydrogen gas with Raney nickel or platinum on charcoal.

This example is repeated using Raney nickel with each of the promoters described herein with similar results.

Example III is successfully repeated by having present 5 parts of water per part of glycoside in the hydrogenation vessel.

EXAMPLE IV

A long chain glucoside is hydrogenated to reduce color according to the following. Butyl glucoside is prepared and transetherified with a $C_{12-13}$ primary alcohol (Neodol 23) to give a long chain glucoside suitable for detergent uses.

This material is hydrogenated in accordance with each of the processes described in Examples I, II and III. Upon conducting the hydrogenation, it is observed that lighter colored products are obtained over the starting glucoside.

EXAMPLE V

Twenty-five parts of a $C_{12-13}$ DP3 glucoside are dispersed in forty parts water. Twenty parts Raney nickel are introduced and the entire mixture is stirred over a period of five hours while maintaining the temperature at 50° C. The color improvement of the hydrogenated composition over the starting material gives a 66% decrease in the extinction coefficient e.g. much higher light transmittance for the finished product.

What is claimed is:

1. A process for reducing the color of a glycoside composition, which process comprises: contacting a colored glycoside composition with hydrogen or a source of hydrogen selected from the group consisting of Raney nickel, lithium aluminum hydride, or sodium borohydride, under catalytic hydrogenation conditions for a suffient time to decrease the color there of and thereafter recovering the glycoside composition of reduced color.

2. The process of claim 1 wherein the glycoside is selected from the group consisting of a fructoside, glucoside, mannoside, galactoside, taloside, aldoside, altroside, idoside, arabinoside, xyloside, lyxoside, and riboside and mixtures thereof.

3. The process of claim 1 wherein in the glycoside is an alkyl glycoside.

4. The process of claim 1 wherein the glycoside is present in the composition on a dry solids basis during hydrogenation at from about 10% to about 75% by weight.

5. The process of claim 2 wherein the glycoside is a glucoside.

6. The process of claim 3 wherein the glycoside contains from about 1 to about 30 carbon atoms in the alkyl radical.

7. The process of claim 1 wherein the temperature of the glycoside composition is maintained between about 10° C. and about 250° C. during hydrogenation.

8. The process of claim 4 wherein the glycoside is present in the composition at from about 20% to about 60% by weight.

9. The process of claim 7 wherein the hydrogenation is conducted at from about 101 KPa to about 10,000 KPa.

10. The process of claim 1 wherein during hydrogenation the glycoside composition is dispersed in a solvent selected from the group consisting of polar and non-polar solvents.

11. The process of claim 10 wherein the solvent is water.

12. The process of claim 10 wherein the solvent is a fatty alcohol.

* * * * *